United States Patent
Wang et al.

(10) Patent No.: US 11,185,220 B2
(45) Date of Patent: Nov. 30, 2021

(54) OPHTHALMOLOGIC APPARATUS

(71) Applicant: Topcon Corporation, Tokyo (JP)

(72) Inventors: Zhenguo Wang, Ridgewood, NJ (US); Zaixing Mao, Tokyo (JP); Hideharu Suzuki, Tokyo (JP); Kazuhiro Oomori, Tokyo (JP); Makoto Fujino, Tokyo (JP)

(73) Assignee: Topcon Corporation, Tokyo (JP)

(*) Notice: Subject to any disclaimer, the term of this patent is extended or adjusted under 35 U.S.C. 154(b) by 56 days.

(21) Appl. No.: 16/845,928

(22) Filed: Apr. 10, 2020

(65) Prior Publication Data

US 2020/0337552 A1 Oct. 29, 2020

Related U.S. Application Data

(60) Provisional application No. 62/837,914, filed on Apr. 24, 2019, provisional application No. 62/837,900, (Continued)

(51) Int. Cl.
*A61B 3/10* (2006.01)
*A61B 3/15* (2006.01)
(Continued)

(52) U.S. Cl.
CPC ............ *A61B 3/101* (2013.01); *A61B 3/0008* (2013.01); *A61B 3/107* (2013.01); *A61B 3/158* (2013.01)

(58) Field of Classification Search
CPC ........... A61B 3/14; A61B 3/0025; A61B 3/12; A61B 3/102; A61B 3/0058; A61B 3/1225;
(Continued)

(56) References Cited

U.S. PATENT DOCUMENTS

| 4,772,116 A | 9/1988 | Schroder et al. |
| 7,278,740 B1 | 10/2007 | Suzuki et al. |

(Continued)

FOREIGN PATENT DOCUMENTS

| JP | S61-500649 A | 4/1986 |
| JP | H07-136120 A | 5/1995 |

(Continued)

*Primary Examiner* — William R Alexander
*Assistant Examiner* — Sharrief I Broome
(74) *Attorney, Agent, or Firm* — Chiesa Shahinian & Giantomasi PC

(57) ABSTRACT

An ophthalmologic apparatus includes: an ophthalmologic apparatus body having: an objective lens that faces a subject's eye; a first illumination optical system that irradiates a cornea of the subject's eye with illumination light emitted from a first illumination light source along an optical axis overlapping an optical axis center of the objective lens; an interference image capturing camera that takes an image of a corneal reflection light through the objective lens and outputs an imaging signal; and a calculation unit that calculates, based on a corneal reflection image, of a corneal reflection light, input from the interference image capturing camera, a thickness of a tear fluid film at each position on the corneal surface; and a guide rail that supports the ophthalmologic apparatus body. The guide rail supports the ophthalmologic apparatus body in a rotatable manner such that an optical axis center of the objective lens is positioned obliquely with respect to a horizontal direction orthogonal to a gravity direction.

8 Claims, 2 Drawing Sheets

Related U.S. Application Data filed on Apr. 24, 2019, provisional application No. 62/837,844, filed on Apr. 24, 2019, provisional application No. 62/844,797, filed on May 8, 2019.

(51) Int. Cl.
*A61B 3/00* (2006.01)
*A61B 3/107* (2006.01)

(58) Field of Classification Search
CPC ..... A61B 3/0008; A61B 3/113; A61B 3/1025; A61B 3/145; A61B 3/0041; A61B 3/0091; A61B 3/103; A61B 3/1005; A61B 3/1015; A61B 3/117; A61B 3/112; A61B 3/107; A61B 3/13; A61B 3/0033; G01B 9/02091; G01B 9/02044; G01B 9/02004; G01B 9/02027; G01B 2290/45; G01B 2290/70; G01B 9/0203; G01B 9/02083; G01B 2290/65; G01B 9/02041; G01B 9/02087; G01B 11/2518; G01B 9/0201; G01B 9/02011; G01B 9/02028; G01B 9/02034; G01B 9/02039; G01B 9/02045; G01B 9/02048; G01B 9/0205; G06T 2207/30041; G06T 2207/10101; G06T 7/0012; G06T 2207/20056; G06T 2207/30104; G06T 5/50; G06T 7/0016; G06T 7/248; G06T 7/337; G06T 15/00; G06T 15/04; G06T 2207/10028; G06T 2207/10048; G06T 2207/10144; G06T 2207/20081; G06T 2207/30096; G06T 2207/30101; G06T 3/0018; G06T 3/0062; G06T 3/4053; G02B 27/141; G02B 26/101; G02B 27/0068; G02B 2027/0187; G02B 26/0833; G02B 27/1013; G02B 7/023; G02B 7/04; G02B 13/0095; G02B 17/006; G02B 17/08; G02B 17/0832; G02B 2027/0118; G02B 2027/0127; G02B 2027/0138; G02B 2027/014; G02B 2027/0178; G02B 2027/0185; G02B 21/0012; G02B 21/0048; A61F 9/007; A61F 2009/00851; A61F 2009/00897; A61F 9/00736; A61F 9/008; A61F 9/00821; A61F 2009/00863; A61F 2009/0087; A61F 2009/00887; A61F 2250/0002; A61F 2/1624; A61F 9/00814; A61F 9/00823; A61F 9/00825; A61F 9/0084; A61F 9/009; A61F 9/013

See application file for complete search history.

(56) References Cited

U.S. PATENT DOCUMENTS

| | | | |
|---|---|---|---|
| 7,413,304 B2 | 8/2008 | Suzuki et al. | |
| 7,661,820 B2 | 2/2010 | Hara et al. | |
| 7,758,190 B2 | 7/2010 | Korb et al. | |
| 7,854,510 B2 | 12/2010 | Verdooner et al. | |
| 7,988,294 B2 | 8/2011 | Korb et al. | |
| 8,591,033 B2 | 11/2013 | Korb et al. | |
| 2004/0212781 A1* | 10/2004 | Mihashi | A61B 3/101 351/221 |
| 2007/0258043 A1 | 11/2007 | Suzuki et al. | |
| 2008/0316499 A1 | 12/2008 | Korb et al. | |
| 2010/0085540 A1 | 4/2010 | Korb et al. | |
| 2010/0315591 A1* | 12/2010 | Gratton | A61B 3/101 351/206 |
| 2011/0285961 A1 | 11/2011 | Korb et al. | |
| 2013/0293842 A1* | 11/2013 | Grenon | G01B 11/0625 351/206 |
| 2014/0240671 A1* | 8/2014 | Korb | A61B 3/101 351/206 |
| 2015/0085252 A1* | 3/2015 | Fujimura | A61B 3/0058 351/208 |
| 2019/0374100 A1 | 12/2019 | Okazaki et al. | |

FOREIGN PATENT DOCUMENTS

| | | |
|---|---|---|
| JP | 3896211 B | 3/2007 |
| JP | 4624122 B2 | 2/2011 |
| JP | 5651119 B2 | 1/2015 |
| JP | 5665181 B | 2/2015 |
| JP | 2019-025257 A | 2/2019 |

\* cited by examiner (a)          (b)

OPHTHALMOLOGIC APPARATUS

BACKGROUND

The present disclosure relates to an ophthalmologic apparatus, and more particularly, to an ophthalmologic apparatus that examines states of an anterior segment and tear fluid film of a subject's eye.

BACKGROUND ART

There has been known an ophthalmologic apparatus that irradiates a cornea of a subject's eye with illumination light, and observes a state of an anterior segment and interference fringes formed by a tear fluid film of the cornea of the subject's eye to make a diagnosis of dry eye, for example.

A tear fluid of the subject's eye flows to a lower side of the cornea in the gravity direction with time. For this reason, there have been known techniques of observing the cornea from the front while illuminating the lower side of the cornea (Japanese Patent No. 3896211, Japanese Patent No. 5665181, and Japanese Unexamined Patent Publication No. 2019-25257).

SUMMARY

It is an object of the present disclosure to provide an ophthalmologic apparatus capable of more accurately examining a state of a tear fluid on a cornea of a subject's eye through photographing a tear fluid film from an obliquely downward direction, even if the tear fluid has flowed to a lower side of the cornea in a gravity direction with time.

An ophthalmologic apparatus of the present disclosure includes: an ophthalmologic apparatus body, including: an objective lens that faces a subject's eye; a first illumination optical system that irradiates a cornea of the subject's eye with illumination light irradiated from a first illumination light source along an optical axis overlapping an optical axis center of the objective lens; an interference image capturing camera that takes an image of a corneal reflection light through the objective lens and outputs an imaging signal; and a calculation unit that detects, based on a corneal reflection image, of a corneal reflection light, input from the interference image capturing camera, wavelength characteristics of an interference image at each position of the corneal reflection image so that a thickness of a tear fluid film at each position on the corneal surface can be calculated; and a guide rail that supports the ophthalmologic apparatus body, wherein the guide rail supports the ophthalmologic apparatus body in a rotatable manner such that an optical axis center of the objective lens is positioned obliquely with respect to a horizontal direction orthogonal to a gravity direction.

The present disclosure can provide an ophthalmologic apparatus capable of more accurately examining a state of a tear fluid on the cornea of the subject's eye through photographing the tear fluid film from an obliquely downward direction, even if the tear fluid has flowed to the lower side of the cornea in the gravity direction with time.

DETAILED DESCRIPTION

Figure 1:
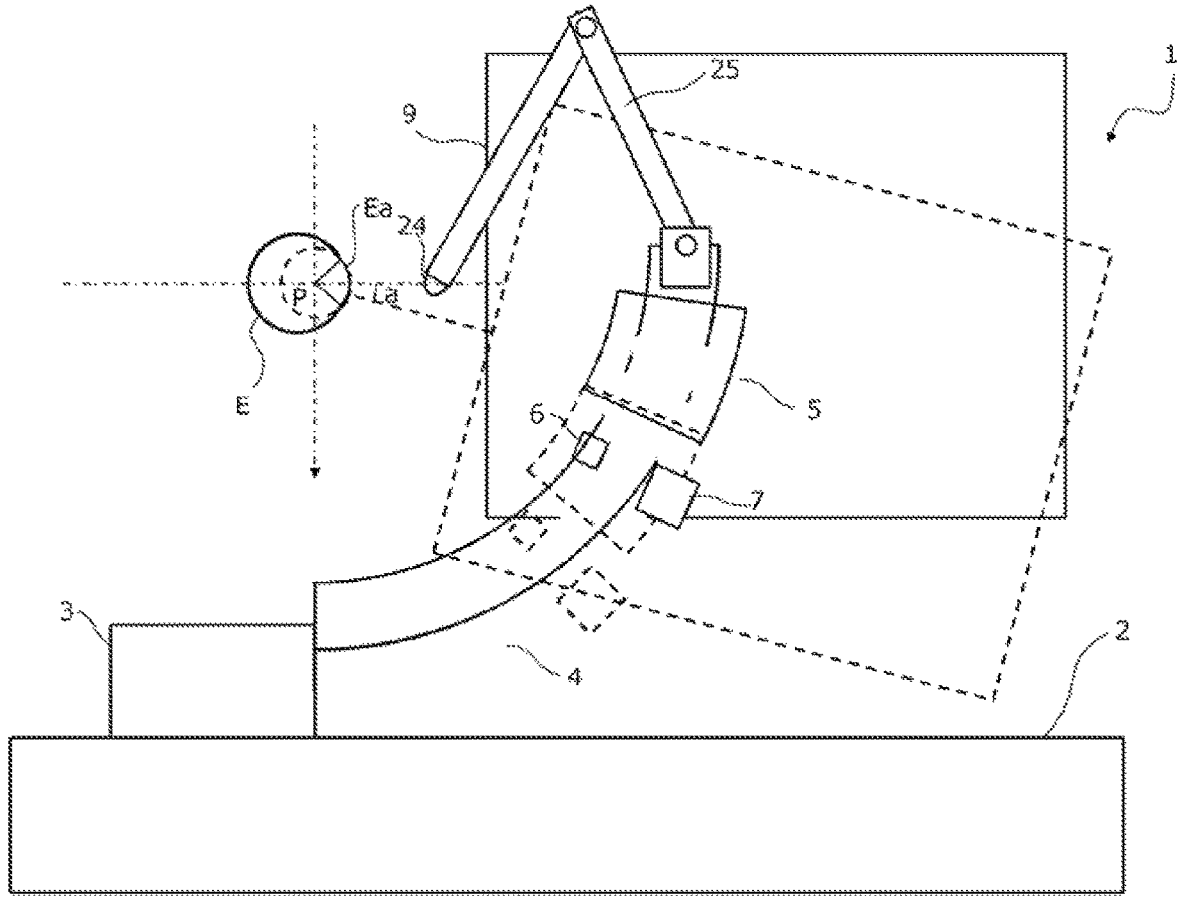
FIG. 1 is a schematic view illustrating an ophthalmologic apparatus according to an embodiment of the present disclosure.

FIG. 1 is a schematic view illustrating an ophthalmologic apparatus 1 according to an embodiment of the present disclosure. The ophthalmologic apparatus 1 includes a base unit 2, a guide rail supporter 3, a guide rail 4, a guide member 5, an encoder (angle detection means) 6, an ophthalmologic apparatus body 9, a fixation lamp 24, and a fixation lamp support arm 25.

The guide rail supporter 3 arranged on the base unit 2 is provided with the guide rail 4 that is curved with a curvature having a point P as a center. Specifically, it is assumed that the subject's eye E is positioned above the guide rail supporter 3 and the point P serves as a center of curvature of the cornea Ea of the subject's eye E at the time of ocular examination. The guide rail 4 has a substantially quarter arc shape that is curved from a lower position of the point P in a gravity direction to a plane horizontally crossing the point P. The guide rail 4 includes the guide member 5 attached thereto and movable along the guide rail 4. The ophthalmologic apparatus body 9 is fixed to the guide member 5. In this manner, moving the guide member 5 along the guide rail 4 makes the ophthalmologic apparatus body 9 rotate about the point P as a center. That is, making the point P as the center of curvature of the cornea Ea allows for change of an angle at which the ophthalmologic apparatus body 9 is directed to the cornea Ea (an angle with respect to the horizontal direction) while maintaining the distance between the cornea Ea and an objective lens 18a, which will be described later. Further, the encoder 6 detecting a rotational angle of the ophthalmologic apparatus body 9 is arranged in the guide member 5. The encoder 6 generates a pulse each time the ophthalmologic apparatus body 9 rotates at a small rotational angle. Further, the ophthalmologic apparatus body 9 is able to drive a driving unit 7 through control from a control unit 10, which will be described later, and move the driving unit 7 along the guide rail 4.

The fixation lamp 24 is a light source that fixes the position of the subject's eye E by guiding the subject's gaze for preferable observation and photographing of the state of the subject's eye E. A light emitting diode (LED) light source or a halogen lamp can be used as the fixation lamp 24. The fixation lamp 24 is attached to the distal end of the fixation lamp support arm 25. The relative position between the fixation lamp 24 and the subject can be freely set.

In FIG. 1, the ophthalmologic apparatus body 9 indicated by the solid line is in a horizontal state. Further, the ophthalmologic apparatus body 9 indicated by the dotted line is inclined after rotating about the point P as the center at an angle of approximately 15 degrees with respect to the horizontal direction through movement of the guide member 5, which is attached to the ophthalmologic apparatus body 9, along the guide rail 4. This rotational angle of the ophthalmologic apparatus body 9 can be detected using pulses generated by the encoder 6 in accordance with the rotation of the ophthalmologic apparatus body 9.

Figure 2:
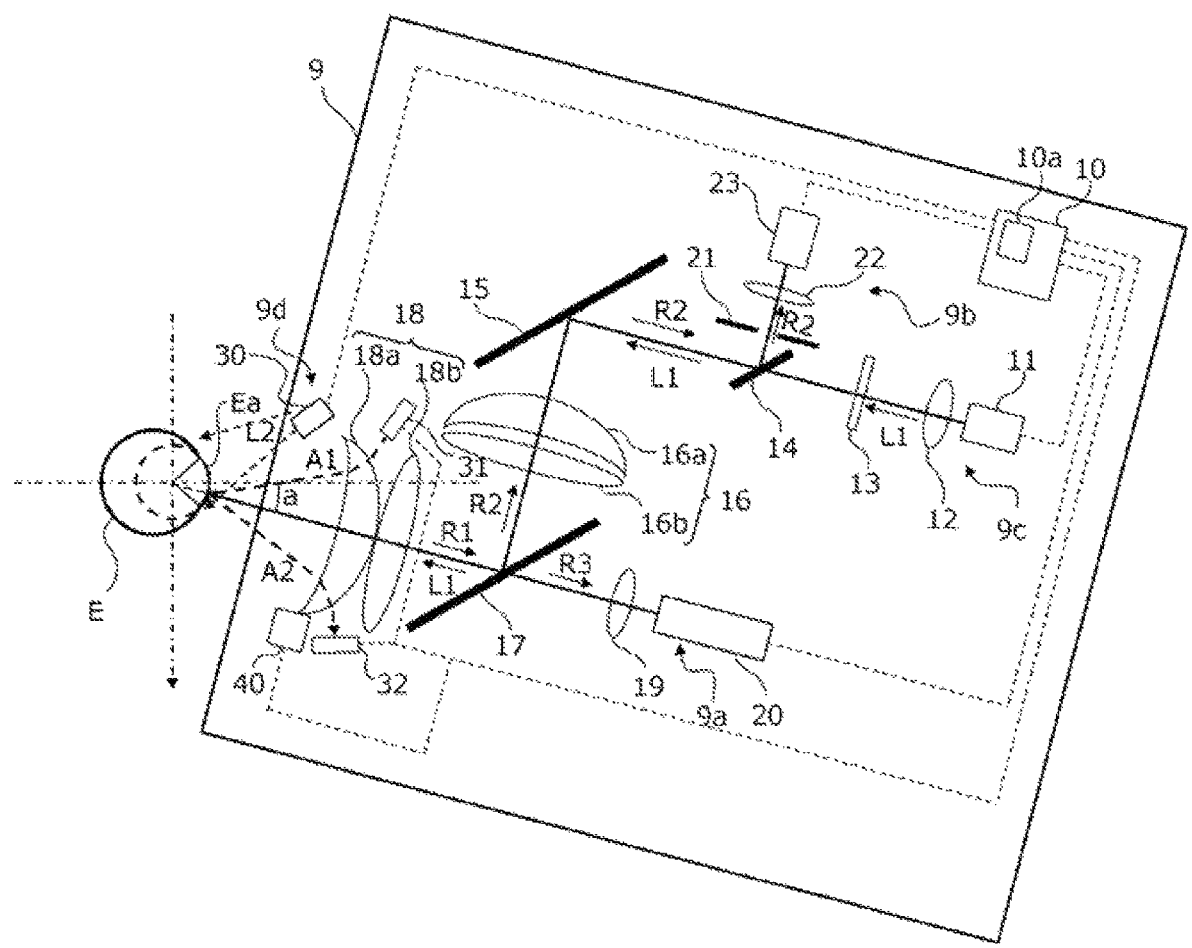
FIG. 2 is a schematic view illustrating an optical system of the ophthalmologic apparatus according to the embodiment of the present disclosure.

FIG. 2 is a schematic view illustrating an optical system of the ophthalmologic apparatus body 9 according to the embodiment of the present disclosure. The optical system of the ophthalmologic apparatus body 9 includes an anterior segment observation optical system 9a, a measurement optical system 9b, a first illumination optical system 9c, and a second illumination optical system 9d.

FIG. 2 shows the ophthalmologic apparatus body 9 according to the embodiment of the present disclosure inclined at an angle of approximately 15 degrees with respect to the horizontal direction.

The anterior segment observation optical system 9a includes a first lens group 18 of the present disclosure. The anterior segment observation optical system 9a includes a third half mirror 17, an imaging lens 19, and an anterior segment camera 20 that are arranged along the direction of an optical axis of the first lens group 18. Note that the term "half mirror" used herein refers to a reflecting mirror that splits light into reflected light and transmitted light at a branching ratio of approximately 1:1, but the present disclosure is not limited thereto.

The first lens group 18 is a so-called objective lens. In the present embodiment, the objective lens (first lens group 18) includes a plurality of lenses (18a, 18b), but the objective lens may include a single lens only. The first lens group 18 may allow the corneal surface of the cornea Ea of the subject's eye E to be irradiated with the illumination light L1 emitted from the first illumination optical system 9c, which will be described later, via the third half mirror 17. Corneal reflection light R1, which is the reflection of the illumination light from the corneal surface, enters the first lens group 18. This corneal reflection light R1 enters the third half mirror 17 from the first lens group 18.

The third half mirror 17 reflects part of illumination light L1 incident from the first illumination optical system 9c toward the first lens group 18. The third half mirror 17 allows part (R3) of the corneal reflection light R1 incident from the first lens group 18 to pass therethrough and exit therefrom toward an imaging lens 19. The third half mirror 17 reflects further part (R2) of the corneal reflection light R1 toward a second lens group 16, which will be described later.

The imaging lens 19 allows the corneal reflection light R3 incident from the third half mirror 17 to pass therethrough and exit therefrom toward the anterior segment camera 20. The anterior segment camera 20 includes a complementary metal oxide semiconductor (CMOS) or charge coupled device (CCD) imaging element, and takes an image of the corneal reflection light R3 incident from the imaging lens 19 to output an imaging signal of an observation image of an anterior segment of the subject's eye E (hereinafter referred to as an "anterior segment observation image") to the control unit 10.

The first illumination optical system 9c includes a first illumination light source 11. The first illumination optical system 9c further includes a lens 12, a filter 13, a first half mirror 14, a second half mirror 15, and a second lens group 16 which are arranged on an optical path of illumination light L1 emitted from the first illumination light source 11. The first illumination optical system 9c shares the third half mirror 17 and the second lens group 16 with the anterior segment observation optical system 9a. The first illumination optical system 9c forms an optical path branching from the anterior segment observation optical system 9a via the third half mirror 17.

The first illumination light source 11 emits light. The first illumination light source 11 may be, for example, a light emitting diode (LED) light source or halogen lamp which emits white light, and emits white light as the illumination light toward the lens 12. Alternatively, an LED having a different wavelength, a laser light source, or a combination of them may also be used. The lens 12 allows the illumination light L1 incident from the first illumination light source 11 to exit therefrom toward the filter 13. The filter 13 adjusts the light intensity and/or wavelength distribution of the illumination light L1 incident from the lens 12, and allows the illumination light L1 thus adjusted to exit therefrom toward the first half mirror 14. Note that the LED may be a bullet-shaped LED. The LED may be replaced with a single halogen lamp or the like.

The first half mirror 14 may allow part of the illumination light L1 incident from the filter 13 to pass therethrough and exit therefrom toward the second half mirror 15. The first half mirror 14 reflects part (R2) of the corneal reflection light R1 incident from the second lens group 16, which will be described later, via the second half mirror 15 toward the measurement optical system 9b, which will be described later.

The second half mirror 15 and the second lens group 16 allow the illumination light L1 incident from the first half mirror 14 to exit therefrom toward the third half mirror 17 described above. Further, the second half mirror 15 and the second lens group 16 allow the corneal reflection light R2 reflected by the third half mirror 17 to exit therefrom toward the first half mirror 14.

In this manner, the corneal surface of the cornea Ea is irradiated with, through the first lens group 18, the illumination light L1 emitted from the first illumination light source 11 and passing through the lens 12 and the third half mirror 17. As a result, the corneal reflection light R1, which is the reflection of the illumination light L1 from the corneal surface, enters the first lens group 18.

The measurement optical system 9b forms an optical path branching from the first illumination optical system 9c via the first half mirror 14. The measurement optical system 9b shares the components from the first lens group 18 to the first half mirror 14 with the first illumination optical system 9c, and also includes a diaphragm 21, a lens 22, and an interference image capturing camera 23.

The diaphragm 21 and the lens 22 allow the corneal reflection light R2 incident from the first half mirror 14 to exit therefrom toward the interference image capturing camera 23.

The interference image capturing camera 23 includes a CMOS or CCD imaging element, and takes an image of the corneal reflection light R2 incident from the lens 22 to output an imaging signal of a corneal reflection image toward the control unit 10.

An alignment adjustment system is used for measuring the alignment of the subject's eye E and the first lens group 18 in an optical axis direction by an optical lever method. The alignment adjustment system is a mechanism including an alignment adjustment unit 40, such as a servo motor, that makes the first lens group 18 movable. Driving the servo motor electrically connected to the control unit 10 to move the first lens group 18 makes it possible to adjust the relative position between the subject's eye E and the first lens group 18 in the optical axis direction, and to adjust the alignment of the optical systems (the anterior segment observation optical system 9a, the measurement optical system 9b, and the first illumination optical system 9c).

A ghost removing light source 30 (second illumination light source) may be, for example, a light emitting diode (LED) light source or a halogen lamp, and is able to emit illumination light L2 toward a corneal surface of the cornea Ea of the subject's eye E. The illumination light L2 irradiated from the ghost removing light source 30 has an optical axis that is shifted from the optical axis of the first lens group 18, which will be described later (second illumination optical system 9*d*).

The control unit 10 is electrically connected to the first illumination light source 11, the anterior segment camera 20, the interference image capturing camera 23, the fixation lamp 24, the ghost removing light source 30, an alignment light source 31, an alignment reflection light receiving unit 32, and the alignment adjustment unit 40.

The control unit 10 includes a calculation unit 10*a*. The calculation unit 10*a* detects, based on the image data of the corneal reflection light R2 (corneal reflection image) input from the interference image capturing camera 23, wavelength characteristics of the interference image at each position of the corneal reflection image so that the thickness of the tear fluid film at each position on the corneal surface can be calculated. The tear fluid film herein refers to an oil layer (lipid layer), an aqueous layer, and a mucinous layer, or a combination of these layers.

The control unit 10 can switch between the first illumination light source 11 and the ghost removing light source 30 (second illumination light source) to irradiate the eye with the illumination light. This enables switching between the mode for reducing ghost and the mode for irradiating the center of the subject's eye E with light in accordance with the examination to be performed.

The ophthalmologic apparatus body 9 shown in FIG. 2 is ready to emit the illumination light with the optical axis center oriented upward at the angle a of approximately 15 degrees with respect to the horizontal direction (direction orthogonal to the gravity direction), and, at the same time, to allow the corneal reflection light to exit downward with the optical axis center oriented downward at the angle a of approximately 15 degrees with respect to the horizontal direction. In this way, the ophthalmologic apparatus 1 can measure a tear fluid film in a certain field of view (hereinafter referred to as "FOV") of the cornea.

Figure 3:
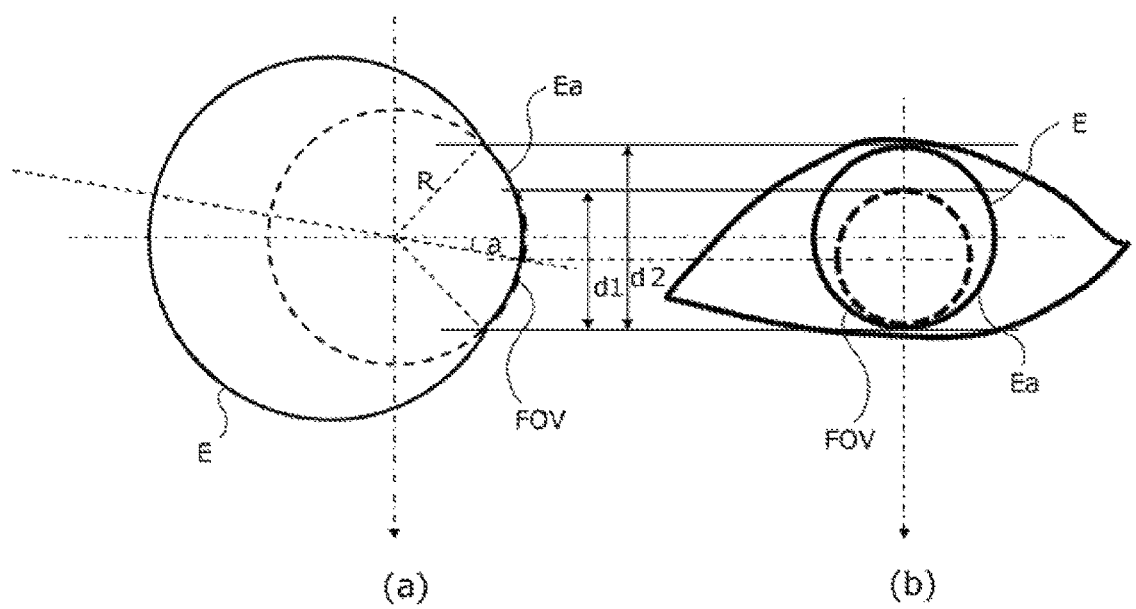
FIG. 3 is a schematic view illustrating a state of a subject's eye according to the embodiment of the present disclosure.

When the subject's eye E is kept open for the measurement, the tear fluid film becomes thin on an upper portion of the subject's eye E due to gravity, and is thickened on a lower portion of the subject's eye E. FIG. 3 is a schematic view illustrating the state of the subject's eye E according to the embodiment of the present disclosure. The diagram (a) of FIG. 3 illustrates the subject's eye E as viewed from the side, and the diagram (b) of FIG. 3 illustrates an eye including the subject's eye E as viewed from the front. The FOV is surrounded by a dotted circle in the diagram of FIG. 3B. Here, the FOV indicated by the dotted circle has a diameter d1 of 5 mm or more, desirably 8 mm or more. For example, when the corneal reflection light exits downward with its optical axis center inclined at the angle a of approximately 15 degrees with respect to the horizontal direction, and if the diameter d1 of the FOV is 8 mm, a vertical dimension d2 of the cornea Ea when viewed from the front is 12 mm, and a radius R of the cornea is 7.7 mm, a lower end of the FOV will be located at the lower eyelid.

With the above configuration, the ophthalmologic apparatus body 9 can rotate about the point P as the center. The point P serves as the center of curvature of the cornea Ea, which makes it possible to change the angle at which the ophthalmologic apparatus body 9 is directed to the cornea Ea while maintaining the distance between the cornea Ea and the objective lens 18*a*. Specifically, the first lens group 18 allows the cornea Ea of the subject's eye E to be irradiated with the illumination light L1 with the optical axis center oriented obliquely upward with respect to the horizontal direction. As a result, the optical axis center of the corneal reflection light R1 reflected from the corneal surface in an obliquely downward direction with respect to the horizontal direction enters the first lens group 18. According to the above-described configuration, even if the tear fluid on the cornea of the subject's eye has flowed to the lower side of the cornea in the gravity direction, the state of the tear fluid film can be accurately examined through photographing the tear fluid film from an obliquely downward direction, with the cornea Ea kept covered with the tear fluid film, so that the thickness of the tear fluid film can be calculated.

Note that the FOV may be larger in size than the cornea Ea. The lower end of the FOV does not need to coincide with the position of the lower eyelid. Therefore, the angle at which the illumination light is irradiated upward with respect to the horizontal direction and the angle a at which the corneal reflection light exits in the horizontal direction are not limited to approximately 15 degrees, and may arbitrarily be set within a range in which the optical axis center of the first lens group 18 forms an angle a of approximately 5 degrees to approximately 25 degrees with respect to the horizontal direction.

Further, it is possible to observe the state in which the tear fluid flows in a predetermined period of time with the subject facing front, and to calculate the angle a in the center of the FOV including the tear fluid flowing, thereby making the ophthalmologic apparatus body 9 rotate at the angle thus calculated.

Furthermore, it is possible to make the ophthalmologic apparatus body 9 rotate stepwise at a predetermined angle from the horizontal direction with the subject facing front, and to calculate the thickness of the tear fluid film each time the rotation of the ophthalmologic apparatus body 9 stops. Specifically, the control unit 10 controls the driving unit 7 to make the ophthalmologic apparatus body 9 rotate, and the calculation unit 10*a* calculates the thickness of the tear fluid film for each rotational angle. Based on the information on the thickness of the tear fluid film for each angle thus obtained, the maximum value, for example, of the tear fluid film can be calculated as the thickness of the tear fluid film.

Moreover, according to the ophthalmologic apparatus 1 of the present disclosure, the light intensity of the illumination light entering the cornea and the light intensity of the corneal reflection light R3, from the cornea, whose image is taken (which is received) by the anterior segment camera 20 or the interference image capturing camera 23 can be used to determine whether or not the optical system of the ophthalmologic apparatus body 9 is located at an appropriate position (angle) with respect to the subject's eye E. Specifically, for example, the ophthalmologic apparatus body 9 rotates stepwise at a predetermined angle from the horizontal direction, and the light intensity of the corneal reflection light R3 is measured each time the rotation of the ophthalmologic apparatus body 9 stops. More specifically, the control unit 10 controls the driving unit 7 to make the ophthalmologic apparatus body 9 rotate, and the calculation unit 10*a* measures the light intensity of the reflection light for each rotational angle. As the light intensity of the corneal reflection light, an imaging signal of the anterior segment camera 20 may be used. The appropriate angle of the ophthalmologic apparatus body 9 is calculated from the relationship between the angle and the light intensity of the reflection light. Making the ophthalmologic apparatus body 9 rotate at this angle allows for an appropriate angle of the ophthalmologic apparatus body 9 with respect to the subject's eye E. In this manner, even in the case of, for example, such a subject (such as an elderly person) whose gaze is likely to be directed downward even when the gaze of the subject's eye E is guided to front by the fixation lamp, the fact that the gaze is directed downward is detected by the ophthalmologic apparatus 1, and the ophthalmologic apparatus body 9 rotates in accordance with the direction of the gaze, thereby making it possible to measure the tear fluid film with good accuracy.

The first illumination light source 11 of the present disclosure is a light source made of a single LED. Therefore, even when the illumination light L1 emitted from the first illumination light source 11 reaches the cornea Ea through the first lens group 18, the shape of a single light source is projected.

In opposition to this, a comparative example will be described now where a plurality of light sources including nine LEDs arranged in a matrix of 3×3 are used as the first illumination light source 11, for example. When the illumination light emitted from the first illumination light source 11 of the comparative example reaches the cornea Ea through the first lens group 18, the light from the plurality of LEDs, i.e., point light sources, is condensed by the first lens group 18 to generate dark portions adjacent to the plurality of LEDs. That is, illuminance difference in the shape of stripes is projected on the cornea Ea as blurred stripes. Therefore, the stripes of the illuminance difference are also generated in the corneal reflection light R1 reflected from the cornea. As a result, the illumination on the cornea of the subject's eye has shades, and the thickness of the tear fluid on the corneal surface may not be correctly measured.

On the other hand, according to the present disclosure, measurement of the cornea is performed under illumination from a single light source. This makes it possible to correctly measure the thickness of the tear fluid on the corneal surface without generating the stripes of the illuminance difference on the cornea.

Furthermore, irradiating the illumination light L2 from the ghost removing light source 30 makes it possible to shift the position of the ghost generated by reflection of the illumination light L2 at the anterior segment away from the optical axis of the anterior segment camera 20. In this manner, ghost can be kept from entering the field of view of the anterior segment camera 20. Hence, it is possible to perform an accurate examination of a cornea or tear fluid film around the center of a subject's eye E, and acquisition of a more correct corneal image.

Note that the ghost removing light source 30 (second illumination light source) from which the illumination light L2 is irradiated may be arranged to have an optical axis along which the illumination light L2 enters the cornea Ea of the subject's eye E from below. Alternatively, the ghost removing light source 30 (second illumination light source) may be arranged to have an optical axis that extends in the horizontal direction with respect to the optical axis center of the first lens group 18.

What is claimed is:

1. An ophthalmologic apparatus, comprising:
   an ophthalmologic apparatus body, including:
      an objective lens that faces a subject's eye;
      a first illumination optical system that irradiates a cornea of the subject's eye with illumination light emitted from a first illumination light source along an optical axis overlapping an optical axis center of the objective lens;
      an interference image capturing camera that takes an image of corneal reflection light through the objective lens and outputs an imaging signal; and
      a calculation unit that detects, based on a corneal reflection image, of a corneal reflection light, input from the interference image capturing camera, wavelength characteristics of an interference image at each position of the corneal reflection image so that a thickness of a tear fluid film at each position on a corneal surface can be calculated; and
   a guide rail that supports the ophthalmologic apparatus body,
   wherein
   the guide rail supports the ophthalmologic apparatus body in a rotatable manner such that an optical axis center of the objective lens is positioned obliquely downward with respect to a horizontal direction orthogonal to a gravity direction.

2. The ophthalmologic apparatus of claim 1, further comprising:
   a driving unit that makes the ophthalmologic apparatus body move along the guide rail; and
   a control unit that controls the driving unit,
   wherein
   the control unit controls the driving unit to makes the ophthalmologic apparatus body rotate, and
   the calculation unit calculates the thickness of the tear fluid film for each rotational angle, and calculates, from the thickness of the tear fluid film thus calculated, a maximum value of the tear fluid film.

3. The ophthalmologic apparatus of claim 1, further comprising:
   a driving unit that makes the guide rail and the ophthalmologic apparatus body move relative to each other; and
   a control unit that controls the driving unit,
   wherein
   the control unit controls the driving unit to make the ophthalmologic apparatus body rotate,
   the calculation unit uses light intensity of the corneal reflection light for each rotational angle to calculate an appropriate angle for measurement, and
   the control unit makes the ophthalmologic apparatus body rotate based on the angle thus calculated.

4. The ophthalmologic apparatus of claim 1, wherein
   the objective lens is configured to allow the subject's eye to be irradiated with the illumination light with the optical axis center oriented obliquely upward with respect to the horizontal direction, and to allow the corneal reflection light to enter thereto with the optical axis center oriented obliquely downward with respect to the horizontal direction.

5. The ophthalmologic apparatus of claim 1, wherein
   the first illumination light source includes a single light source only.

6. The ophthalmologic apparatus of claim 5, wherein
   the first illumination light source is a bullet-shaped LED.

7. The ophthalmologic apparatus of claim 1, further comprising:
   a second illumination optical system that irradiates the cornea of the subject's eye with illumination light emitted from a second illumination light source along an optical axis center different from the optical axis center of the objective lens; and
   a control unit that controls the first illumination light source and the second illumination light source,
   wherein
   the control unit is able to switch between the first illumination light source and the second illumination light source to irradiate the cornea with the illumination light.

8. The ophthalmologic apparatus of claim 7, wherein the second illumination light source emits the illumination light to irradiate the cornea of the subject's eye with the illumination light without passing through the objective lens.

\* \* \* \* \*